(12) United States Patent
Babaeizadeh et al.

(10) Patent No.: US 9,585,617 B2
(45) Date of Patent: Mar. 7, 2017

(54) CAPNOGRAPHY SYSTEM FOR AUTOMATIC DIAGNOSIS OF PATIENT CONDITION

(75) Inventors: Saeed Babaeizadeh, Arlington, MA (US); Eric Helfenbein, Sunnyvale, CA (US); Dawn Butler, Andover, MA (US); Sophia Huai Zhou, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 800 days.

(21) Appl. No.: 14/000,535

(22) PCT Filed: Feb. 22, 2012

(86) PCT No.: PCT/IB2012/050807
§ 371 (c)(1),
(2), (4) Date: Aug. 20, 2013

(87) PCT Pub. No.: WO2012/114286
PCT Pub. Date: Aug. 30, 2012

(65) Prior Publication Data
US 2013/0324873 A1 Dec. 5, 2013

Related U.S. Application Data

(60) Provisional application No. 61/576,907, filed on Dec. 16, 2011, provisional application No. 61/445,192, filed on Feb. 22, 2011.

(51) Int. Cl.
*A61B 5/08* (2006.01)
*A61B 5/00* (2006.01)
(Continued)

(52) U.S. Cl.
CPC ............ *A61B 5/4848* (2013.01); *A61B 5/082* (2013.01); *A61B 5/0826* (2013.01); *A61B 5/0836* (2013.01); *A61M 16/0051* (2013.01); *A61M 16/04* (2013.01); *A61B 5/0816* (2013.01); *A61M 2016/0413* (2013.01); *A61M 2230/06* (2013.01); *A61M 2230/205* (2013.01); *A61M 2230/30* (2013.01); *A61M 2230/432* (2013.01)

(58) Field of Classification Search
CPC .............................. A61B 5/4848; A61B 5/082
See application file for complete search history.

(56) References Cited

U.S. PATENT DOCUMENTS

| | | | |
|---|---|---|---|
| 5,598,508 | A | 1/1997 | Goldman |
| 6,428,483 | B1 | 8/2002 | Carlebach |

(Continued)

FOREIGN PATENT DOCUMENTS

| | | |
|---|---|---|
| CN | 1279599 A | 1/2001 |
| CN | 2435050 Y | 6/2001 |

(Continued)

*Primary Examiner* — Christian Jang

(57) ABSTRACT

An improved medical capnography system (22) automatically determines the effect of therapy on the underlying patient. The system enable the determination of proper endotracheal tube or advanced airway placement, the effectiveness of CPR, and the occurrence of the return of spontaneous circulation (ROSC) or loss of spontaneous circulation by use of a therapy analyzer (36) implementing an analyze therapy algorithm (336). The system may be implemented in platform-independent hardware or software.

17 Claims, 9 Drawing Sheets

(51) Int. Cl.
  *A61B 5/083* (2006.01)
  *A61M 16/00* (2006.01)
  *A61M 16/04* (2006.01)

(56) References Cited

U.S. PATENT DOCUMENTS

| | | |
|---|---|---|
| 8,660,971 B2 | 2/2014 | Orr |
| 8,939,922 B2 | 1/2015 | Strand et al. |
| 9,039,629 B2 | 5/2015 | Zhou et al. |
| 2011/0040713 A1 | 2/2011 | Colman et al. |
| 2012/0140005 A1 | 6/2012 | Devoeght et al. |
| 2013/0324873 A1 | 12/2013 | Babaeizadeh et al. |

FOREIGN PATENT DOCUMENTS

| | | |
|---|---|---|
| WO | 2010052608 A1 | 5/2010 |
| WO | 2010150239 A1 | 12/2010 |
| WO | 2011154948 A1 | 12/2011 |

Fig. 8
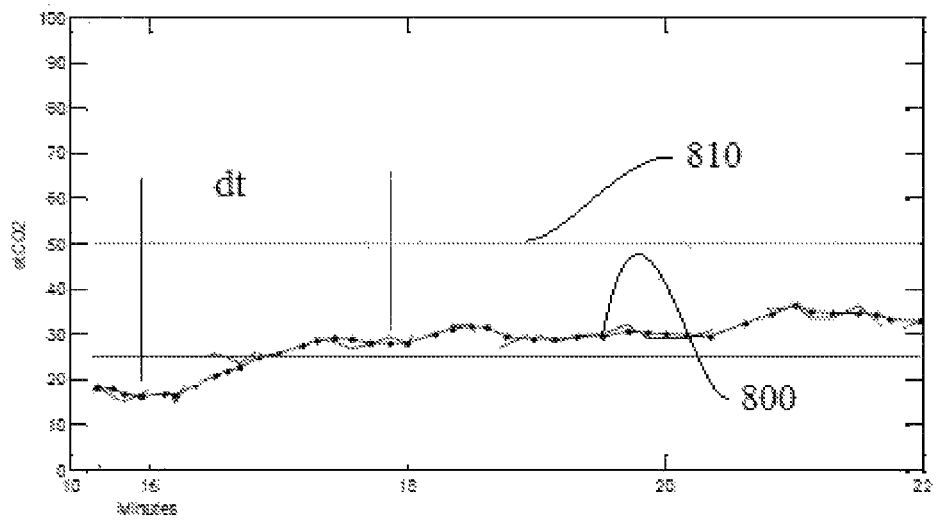
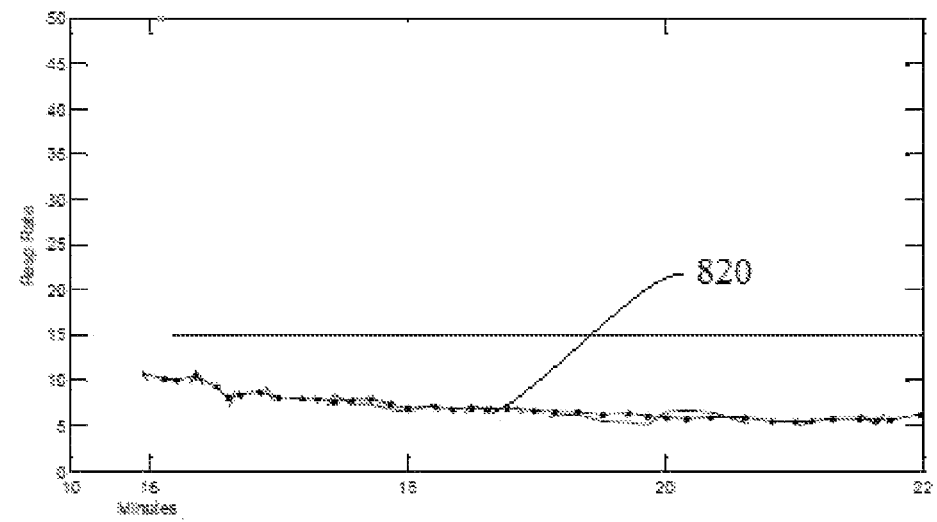

CAPNOGRAPHY SYSTEM FOR AUTOMATIC DIAGNOSIS OF PATIENT CONDITION

CROSS-REFERENCE TO PRIOR APPLICATIONS

This application is the U.S. National Phase application under 35 U.S.C. §371 of International Application No. PCT/IB2012/050807, filed on 22 Feb. 2012, which claims the benefit of U.S. Provisional Patent Application No. 61/576907, filed on 16 Dec. 2011 and U. S. Provisional Application No. 61/445192 filed on 22 Feb. 2011. These applications are hereby incorporated by reference herein.

This invention relates to an improved medical carbon dioxide ($CO_2$) monitoring system and, in particular, to a $CO_2$ monitoring system that automatically determines the effectiveness of intubation or other advanced airway placement therapy or cardiopulmonary resuscitation (CPR) therapy, or respiration therapy as applied to the patient. Respiration therapy could include monitoring the response to a bronchodilator medication for obstructive airway disease, such as asthma. The effectiveness of such therapy can be seen in the changing shape of the $CO_2$ waveform. The system also determines the occurrence of the return of spontaneous circulation (ROSC) during treatment.

$CO_2$ monitoring systems are presently employed in hospital surgical suites and intensive care units to monitor a patient's respiration. Generally these systems are sophisticated and sizeable ventilation systems which monitor the patient's oxygen intake and respiratory $CO_2$. However, there are other scenarios where more advanced $CO_2$ monitoring is desirable. One scenario is intubation or advanced airway placement, where air is being supplied to a patient by a respiration device the end of which is inserted into the patient's airway. Another is the application of CPR to a patient stricken by cardiac arrest. Another is when a person is in respiratory distress, such as from obstructive airway disease e.g., asthma, and respiratory therapy, such as a bronchodilator medication, is being applied while their expired $CO_2$ is being monitored. A portable unit is desirable in such situations, such as the MRx defibrillator monitor produced by Koninklijke Philips North America {Andover, Mass.}, which may be used in a hospital but is portable and can be taken to the site of an accident or location of a stricken patient. It would be desirable for such a portable monitor to be capable of monitoring the $CO_2$ expiration of a patient and interpreting the $CO_2$ waveform in order to determine the effectiveness of the treatment applied in each of these situations.

For example, intubation is a notoriously difficult procedure that if applied in error can be fatal to the patient. Unrecognized esophageal intubation, in which the tube is mistakenly routed into the digestive tract instead of to the lungs, is a great danger in pre-hospital airway management and can lead to the long-term sequelae of anoxic brain injury and death. In some instances, even if the patient has been initially intubated correctly in the field, the endotracheal tube (ETT) may migrate out of the trachea during transport to the emergency department. In one study, the overall misplaced airway rate for patients arriving at the emergency department was an alarming 25% of which 16.7% were esophageal. In addition, the observational methods to confirm correct placement of the ETT have been shown to be unreliable. The use of supraglottic advanced airways has reduced the prevalence of mis-intubations, but these devices may also be misplaced with subsequent disastrous consequences.

Death by hyperventilation is another common and life-threatening airway management problem that arises during cardiopulmonary resuscitation. At least one study has shown that despite seemingly adequate training, professional rescuers consistently hyperventilate patients during out-of-hospital CPR. The study also indicated that excessive ventilation rates significantly decrease coronary perfusion pressures and survival rates. Unrecognized and inadvertent hyperventilation may be contributing to the currently dismal survival rates from cardiac arrest. In the presence of CPR, determination of ventilation rate can be performed more accurately using the $CO_2$ waveform than the commonly used impedance method, and when combined with analysis of end-tidal $CO_2$, this can be an effective method for detection of inadvertent hyperventilation. Hyperventilation in the presence of traumatic brain injury is also extremely detrimental, and may result in cerebral ischemia.

Effective CPR is universally recognized as a critical treatment for cardiac arrest victims. Although CPR is commonly applied, its quality is often poor due to inadequate training or caregiver fatigue. What is needed is a real-time indication to the caregiver of whether or not the applied CPR is effective. If the CPR is not effective, the caregiver can be guided to improving the technique. The inventors have recognized that one indicator of CPR quality may lie in the patient's expired $CO_2$ profile.

Each of the above described treatments, if successful, will result in a return of spontaneous circulation (ROSC). It would also be desirable for a portable monitor that automatically recognizes the occurrence of ROSC and provides an indication of such to the rescuer. Similarly, loss of spontaneous circulation after ROSC may be initially detected as a sudden drop in the $etCO_2$ values, and would be an indication to resume CPR.

Patients in respiratory distress, such as from obstructive airway diseases such as emphysema, asthma, chronic bronchitis or cystic fibrosis, are often provided medication such as bronchodilators to open their airways. The shape of the $CO_2$ waveform can be used to both diagnose obstructive airway, and to monitor the effectiveness of treatment.

$CO_2$ analyzing technology, or capnography, is currently used for determining a patient condition based on the trending of the patient's $CO_2$ expiration. The prior art and co-assigned patent application, entitled "Carbon Dioxide Monitoring System" (WO2010/052608), describes a capnographic monitor which is implemented in a portable monitoring device to provide $CO_2$ monitoring and interpretation during intubation, advanced airway placement, CPR treatment, or ventilation. The device incorporates an input setting to identify the particular treatment being applied to the patient, so that the monitor is sensitive to the respiratory condition which may be expected during that treatment.

From the above described problems, the inventors have realized that what is needed is an improved capnography system which provides feedback as to the effectiveness of cardiovascular therapies. The improvements in the system relate to the automatic detection of breaths, discrimination of true breaths from artifact, and therapy analysis which takes into account physiological trends in the patient's $CO_2$ expiration during the therapy.

It is in accordance with the principles of the present invention to describe a system for providing clinical decision support, and in particular by analyzing $CO_2$ waveforms in order to aid clinicians with the decision making process during cardiac-and respiratory-related rescues. The system may be implemented in a software scalable algorithm that can operate at appropriate levels to match user needs with the processing hardware. An algorithm of the system analyzes the patient's CO2 waveform and produces parameters and events. The results of the analysis are either directly reported or may be used to report a relevant clinical statement.

The software algorithm is preferably designed to be machine (host) independent and can, therefore be used in more than one operating environment. The common source code of the algorithm can be configured to achieve the appropriate level of functionality and to conform to the operating environment of the host device. The algorithm includes specified interfaces for CO2 signal input, controls, and output signals as well as operating environment specifications.

It is thus an object of the present invention to provide a system in which a CO2 monitoring method is integrated into a portable monitoring device for use in the hospital or in ambulatory settings, where lifesaving cardiovascular rescue techniques are commonly employed. The method may optionally be implemented in a machine-independent software algorithm such that the method may be used by any computer processor and operating system hardware.

Another object of the present invention is to provide a CO2 monitoring system which processes and analyzes the variation of CO2 during respiration to provide useful treatment information to a caregiver. The system uses a CO2 sensor that produces a signal which is a measure of the CO2 level of a patient's respiration. The CO2 signal is digitized and recorded by the CO2 monitor. The CO2 signal stream is optionally analyzed for noise content and the noise level reduced to produce a "clean" CO2 signal. Various characteristics of the waveform, such as corners and peaks, are detected and measured. The characteristics are applied to an artifact detector to determine and remove artifact from true breaths. The stream of true breaths is then analyzed to identify the likely treatment being provided and the treatment's effectiveness. If an adverse respiratory condition is found, the monitor may issue an audible or visible alarm and/or may issue a clinical advisory statement by means of a display or annunciator.

Another object of the present invention to provide a system for determining the effectiveness of treatment during intubation, advanced airway placement, or CPR by means of the patient's expiration of CO2. The system comprises a novel use of end-tidal CO2 readings over a sequence of true breaths to determine if the patient is improving during the treatment, or if the endotracheal-tube or advanced airway has been properly placed.

Another object of the invention is to provide a system for identifying the occurrence of the return of spontaneous circulation (ROSC), or the loss of spontaneous circulation. The method may be incorporated into a medical rescue device such as a defibrillator.

In the Drawings:

FIG. 8 illustrates in graphical form a measured etCO2 signal and calculated respiration rate, used in a method for determining the effectiveness of CPR.

Figure 1:
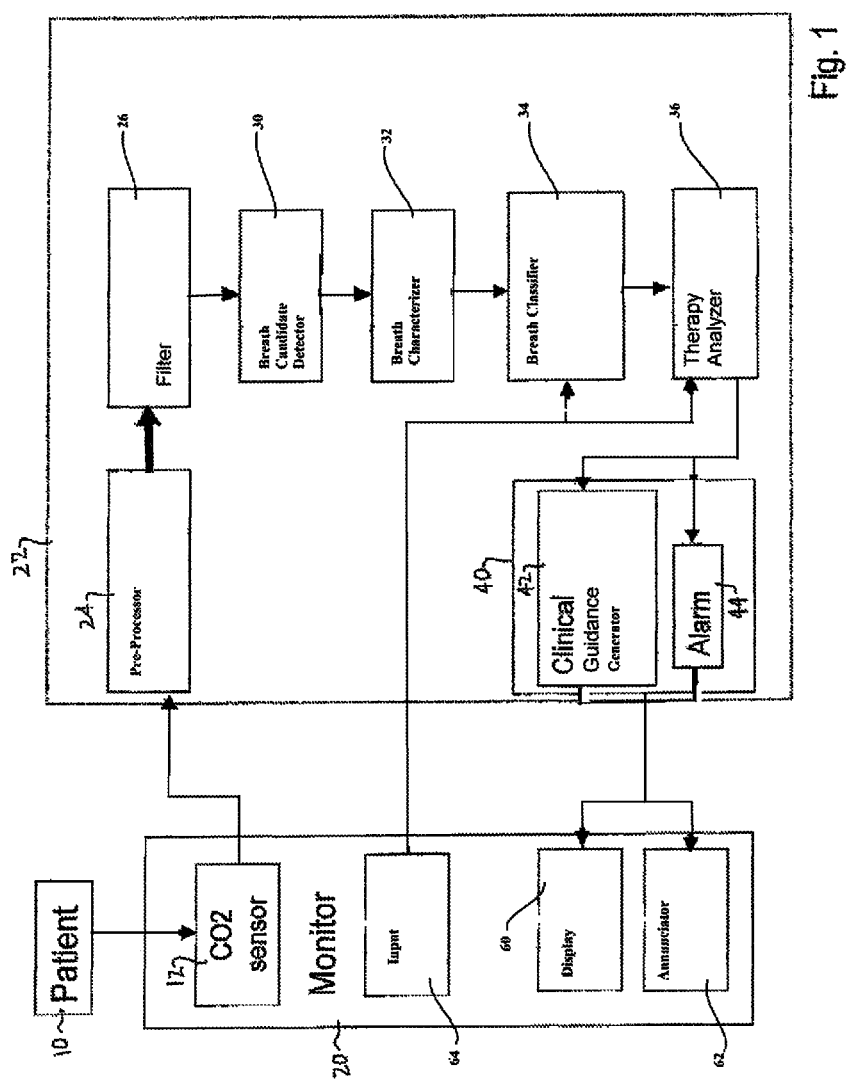
FIG. 1 illustrates in block diagram form a CO2 monitoring system of the present invention that is operatively connected to a patient.

Referring first to FIG. 1, a CO2 monitoring system 14 including a CO2 monitor 20 and a CO2 analyzer 22 is shown in block diagram form. A CO2 monitor is shown being used to monitor a subject patient 10. CO2 monitor 20 is capable of monitoring CO2, and may also be capable of monitoring other patient functions, such as blood pressure, blood oxygen, ECG and the like. CO2 monitor 20 may also comprise controls, display and indicator lights, and aural alarms and prompts.

The patient's respiratory gases are provided to a CO2 sensor 12 within CO2 monitor 20. CO2 sensor 12 senses the CO2 gas concentration in the subject's expiration. The CO2 measurement signals from the sensor 12 are conveyed to a CO2 processor 22. The CO2 processor 22 is shown in FIG. 1 as residing separate from the CO2 monitor 20. However, the invention is not so limited. CO2 processor 22 may reside within the monitor 20, may be a separate apparatus, or may alternatively be constructed as a software module.

CO2 processor 22 comprises a pre-processor 24 which digitizes the CO2 signals into a stream of samples and stores the stream in a computer memory for later use. The digitized CO2 signal stream represents a continuous CO2 waveform. The waveform is preferably a variation with time of CO2 in mmHg Exemplary CO2 signal streams are shown in FIGS. 2, 4, 5, 6, 8, and 9.

The CO2 signal stream output from pre-processor 24 may optionally be processed to reduce noise content at a noise reduction filter 26. One technique for analyzing the noise content at filter 26 is to analyze the high frequency content of the CO2 signal stream. A clean CO2 waveform will exhibit relatively little high frequency content. Filter 26 may thus comprise a digital low pass filter which reduces the signal stream noise level.

The digitized and filtered CO2 signal stream undergoes a first waveform detection at breath candidate detector 30. One technique for detecting a CO2 breath candidate is to detect the difference in successive CO2 samples, which effectively detects the slope of the CO2 waveform. Referring to the example breath candidate sequence 100 at FIG. 2, a steeply rising slope 108 which passes from a background noise threshold level 104 is a characteristic of either the beginning of a patient exhalation, or may be indicative of an artifact event. A further indication of an exhalation or artifact event is a steeply falling slope 110 which passes below the background noise threshold level 104. The breath candidate detector 30 thus operates to identify a time sequence of breath candidates such as breath 1 and breath 2, separated by a period of inactivity.

Still referring to FIG. 1, the sequence of breath candidates is next processed by breath characterizer 32. Breath characterizer 32 determines a set of characteristics for each breath candidate. These characteristics may include the baseline of the waveform candidate, the amplitude of the waveform, the frequency of the waveform with regard to the previous candidate, the rhythm of the waveform, the corners of the waveform, the slopes of the waveform, and characteristics of the shape of the waveform.

The breath candidate characteristics are classified at breath classifier 34 to assess whether each candidate waveform is a respiration waveform or artifact. In particular, artifact generated as a result of external CPR compressions has distinguishing characteristics from true breath waveform shapes. Breath classifier 34 analyzes the breath candidates accordingly, and segregates true breaths from artifact. A therapy input 64 may optionally communicate a treatment identifier to breath classifier 34 in order to improve the accuracy of the analysis. The method of distinguishing artifact from true breaths will be discussed in more detail below.

Breath classifier 34 conveys a sequence of true breaths to therapy analyzer 36. Therapy analyzer 36 operates to determine the effectiveness of the underlying patient therapy based on the trending of at least two true breaths. Exemplary determinations are the effectiveness of CPR, the proper placement and/or continued proper placement of an endotracheal tube (ETT) or advanced airway, and the occurrence of a return of spontaneous circulation (ROSC) during the rescue therapy. In addition, the incidence of hyper- or hypo-ventilation during CPR can be determined by therapy analyzer 36.

Therapy input 64 may optionally be provided to therapy analyzer 36 in order to improve the accuracy of the analysis. For example, a start time for intubation or airway placement, or of initiation of bronchodilator therapy may be conveyed by a user input, such as a therapy input switch. The start time is useful in the airway placement analysis, as described in more detail below, The effectiveness of the patient therapy as determined by therapy analyzer 36 may be communicated back to the user via an output generator 40 in several ways. Display 60 may provide an output instruction as generated by clinical guidance generator 42, or may display alarms or alerts as generated by alarm 44. An annunciator 62 may provide audible instructions from clinical guidance generator 42, or alarm signals from alarm 44. Although display 60 and annunciator 62 are shown in FIG. 1 as residing in monitor 20, it is understood that either may be disposed in analyzer 22 or in a completely different location such as a networked central monitoring location. The clinical guidance instruction advises the user that a particular problem or difficulty should be investigated, or alternatively that the patient is improving. Output instructions such as "no respiration received" or "erratic CO2 waveform" may be generated to indicate a malfunction or erroneous use.

When the CO2 monitoring system 20 is coupled to the patient, it should be set to identify the treatment being applied to the patient, such as intubation, CPR, or ventilation. This may be done by a manual switch or input to the monitoring system which set by the clinician. The setting may also be done automatically by the particular treatment device being used. For instance, when the air conduit of an intubation device is connected to the CO2 monitor 20, the monitor may sense the connection of the air conduit and thereby is informed that intubation is being monitored. For CPR a CPR pad which is placed on the chest of the patient and depressed during CPR may be connected to the monitor 20 and so inform the monitor that CPR is being performed. During ventilation the ventilator or its air conduit may be connected to the monitor 20 to inform the monitor that ventilation is being performed. The identification of the treatment regimen will condition the monitor 20 to be particularly sensitive to respiratory conditions which may be expected during the treatment regimen being applied. This automatic identification of treatment may be supplied in addition to or alternative to the therapy input 64.

Figure 2:
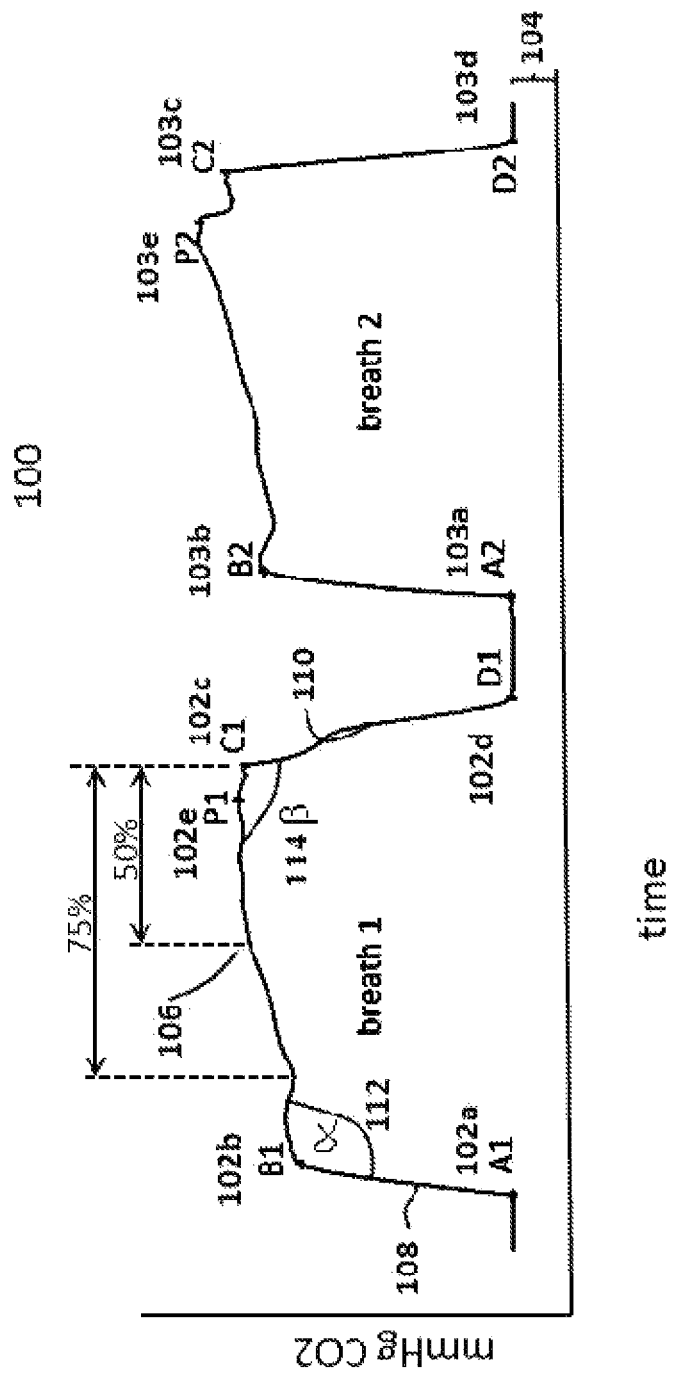
FIG. 2 illustrates the parameters of a typical breath candidate portion of a CO2 signal.

FIG. 2 illustrates the standard parameters of a normal CO2 waveform 100. When the patient exhales and the expiration phase begins, the waveform will rise from a background noise level 104 which represents a baseline CO2 value with a steep slope 108 until a sustained plateau level 106 of CO2 content of the exhaled air is attained. The waveform 100 will exhibit a corner alpha 112 when the sustained level is reached. When the patient finishes exhaling the waveform will drop from a corner beta 114 along a downstroke falling slope 110 to the signal the start of the next inspiration phase. The waveform will then repeat in this manner at the frequency and periodicity of the patient's respiration.

Figure 3:
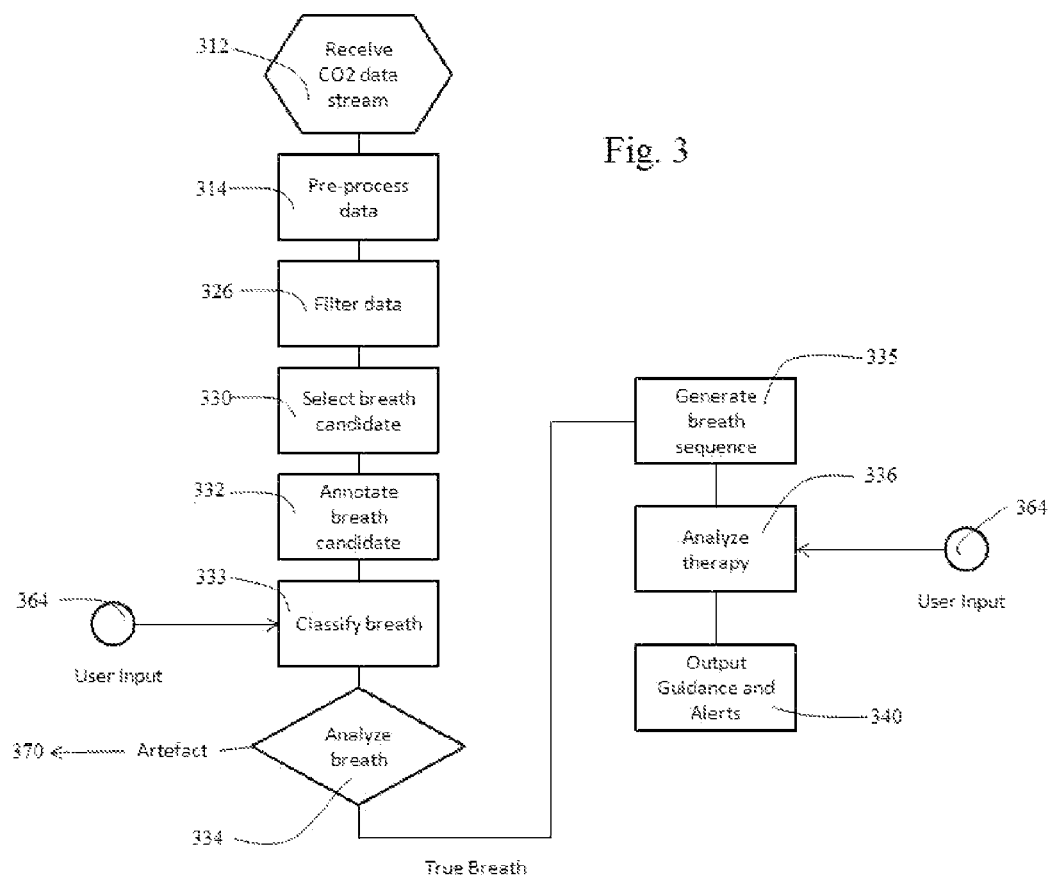
FIG. 3 illustrates a flow chart of the method of determining the condition of a patient from a capnography waveform.

The shape of the CO2 breath waveforms in FIG. 2 contains other identifiable and useful characteristics. Waveform corners 102a, 102b, 102c, 102d, 103a, 103b, 103c, and 103d define the major events of exhalation and inhalation. Maximum amplitude points 102e and 103e define the end-tidal CO2 (etCO2) values for each breath. The plateau shape 106, or portions of the plateau shape 106, may be an indicator of a true breath. These may also be used to determine the presence of acute airway obstruction. The above described parameters can easily be used to determine breath characteristics such as waveform baseline, waveform amplitude, waveform frequency, waveform slope, and waveform rhythm FIG. 3 illustrates a method of using a capnography system for providing information to the user to guide clinical treatment decisions. The method is initiated when CO2 data is received in step 312 from a patient-worn CO2 sensor. The CO2 data is digitized and stored at step 314, and optionally filtered to reduce noise at step 326. The output of step 326 is a CO2 waveform which encompasses a sequence of breaths from the patient.

Breath candidates are selected from the CO2 waveform at step 330. Referring back to FIG. 2, step 330 may incorporate a technique for detecting a CO2 breath candidate by detecting the difference in successive CO2 samples, thus effectively detecting the slope of the CO2 waveform. Referring to the example breath candidate sequence 100 at FIG. 2, a steeply rising slope 108 which passes from a background noise threshold level 104 is a characteristic of either the beginning of a patient exhalation, or may be indicative of an artifact event. A further indication of an exhalation or artifact event is a subsequent steeply falling slope 110 which passes below the background noise threshold level 104. The breath candidate detector 30 thus operates to identify a time sequence of breath candidates such as breath 1 and breath 2, separated by a period of inactivity. The resulting sequence of breath candidates is then provided to the annotate breath candidate step 332 for further processing.

Parameters for the sequence of breath candidates are calculated at step 332. The corners 102a-d, peak value 102e, plateau 106 slope, upstroke 108 slope, downstroke 110 slope, baseline value 104, sequence frequency and stability of rhythm are determined. The parameters are then passed to the classify breath step 333.

Figure 4:
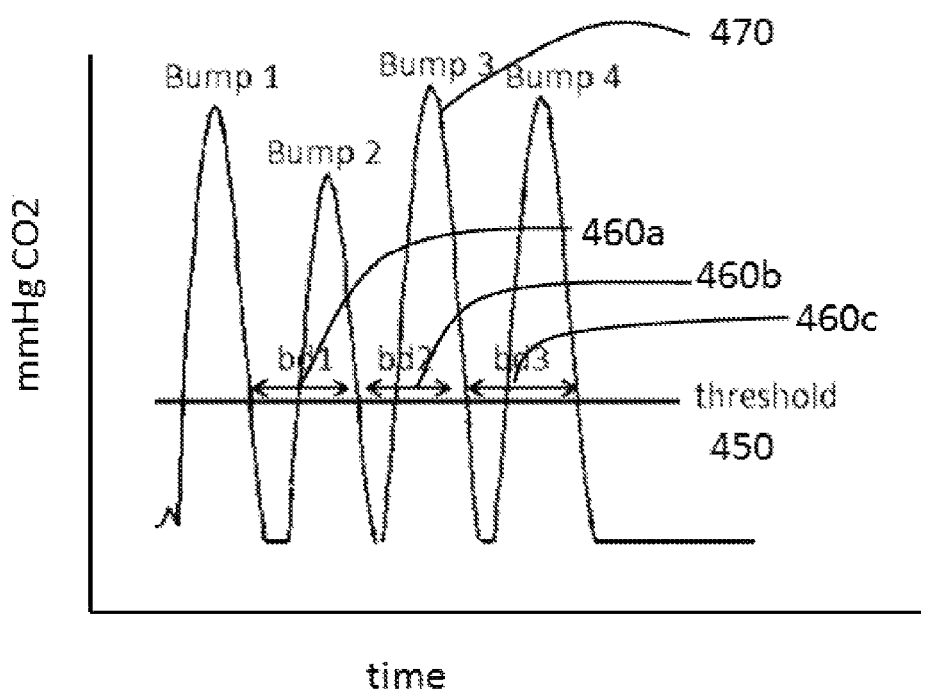
FIG. 4 illustrates an artifact breath sequence of a CO2 signal for a patient undergoing CPR compressions.

Breaths are classified as artifact or true breath at step 333. One source of artifact in the CO2 signal stream is introduced during CPR. CPR is performed by applying chest compressions at a rapid rate, generally about 100 compressions per minute. These rapid but firm compressions will cause the lungs to be compressed and recoil from compressions in short, high frequency increments, which causes some gases to be cycled through the lungs. CPR artifact may thus exhibit a shape similar to a typical breath, FIG. 2, or may appear as "bumps" 470 as shown in FIG. 4.

Step 333 distinguishes artifact by the following algorithm. Accuracy of the algorithm may be increased by means of a user input 364, such as a button or CPR force sensor signal when CPR is being administered. In the case of a CO2 waveform having the general shape of FIG. 2, CPR artifact is determined for breath 2 if $$time(103a-102c) < T1*(\text{average breath gap})$$

AND $$time(103d-103a) < T2,$$

where T1 is a fixed fraction of the average breath gap having a range from about 0.4 to 0.5, the average breath gap is a dynamic value updated with every true breath, and T2 is a fixed interval of duration for a reasonable breath having a value of about 600 milliseconds.

In the case of a CO2 waveform breath candidate having the multiple bump shape 470 of FIG. 4, CPR artifact is determined if the greatest bump interval 460a, 460b, or 460c is shorter than 550 milliseconds. The bump interval is measured where the CO2 waveform 470 crosses a threshold line 450 equal to 75% of the average of the peak-peak bump amplitudes.

The breath candidates which are classified as artifact are segregated from the breath candidates classified as true breaths at step 334. Artifact breath candidates are normally not discarded. Further analysis of the artifact candidates may occur at step 370 to provide an output instruction that CPR is being administered, or to obtain end-tidal CO2 readings indicating whether CO2 is being exchanged in the lungs during CPR. Such readings are useful to determine the effectiveness of CPR.

Figure 5:
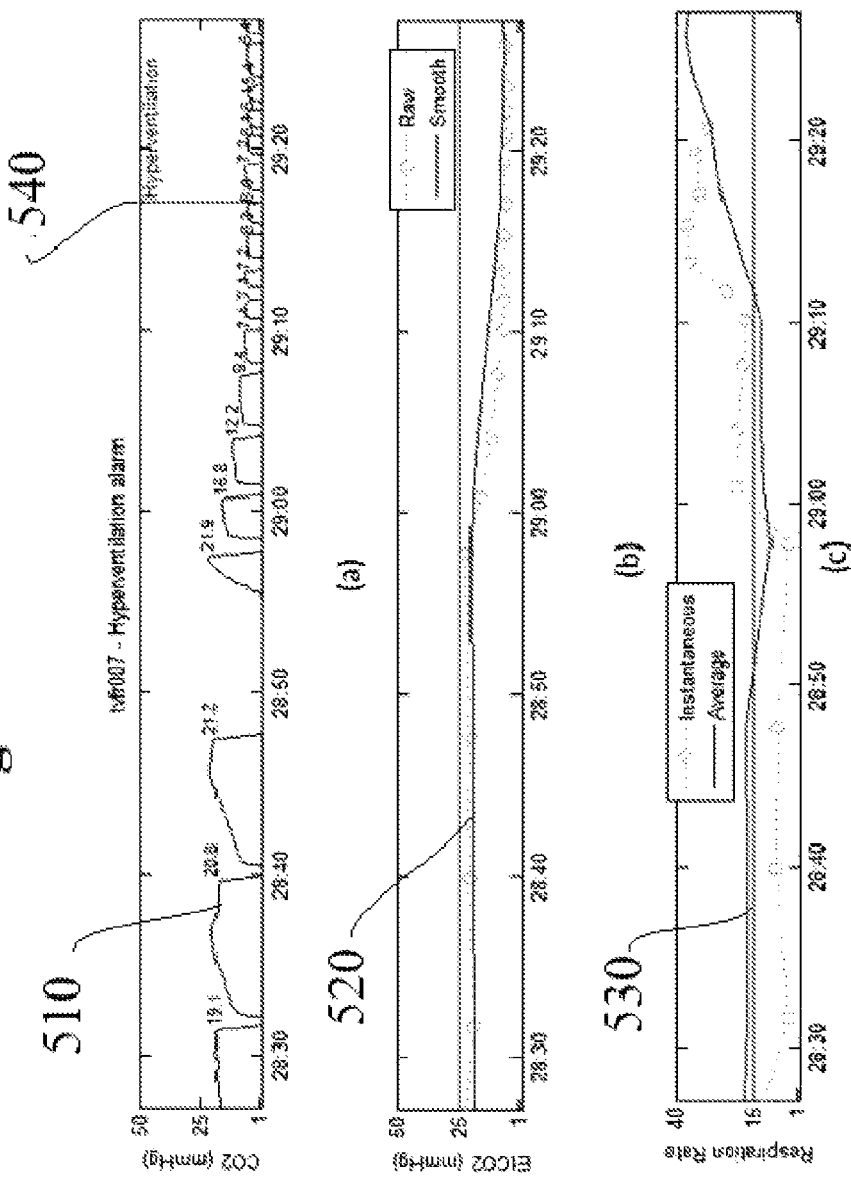
FIG. 5 illustrates a typical breath sequence of a CO2 signal juxtaposed with a calculated end-tidal CO2 (etCO2) trend and respiration rate trend which may be produced from a patient who is being inadvertently hyperventilated.

True breaths are passed from step 334 to the generate breath sequence step 335. In step 335, the true breaths are further processed to determine parameters such as an end-tidal CO2 trend curve 520 and a respiration rate trend curve 530. Referring now to FIG. 5, curve 520 may be calculated by known methods such as by a running mean of true breath etCO2 values. Respiration rate trend curve 530 may be calculated by known methods such as by a running occurrence rate of true breaths, as shown by CO2 ventilation signal stream 510. The output of these values is communicated to the analyze therapy step 336.

Analyze therapy step 336 determines whether the underlying therapy is effective or defective in some way. A first determination is for the hyperventilation case. FIG. 5 shows that a respiration rate 530 greater than a threshold such as 15 breaths per minute in combination with a declining etCO2 value at 520 is an indicator of hyperventilation condition 540. In such a state, a hyperventilation signal is provided to the output guidance and alerts step 340 to alert the rescuer to reduce ventilations.

Figure 6:
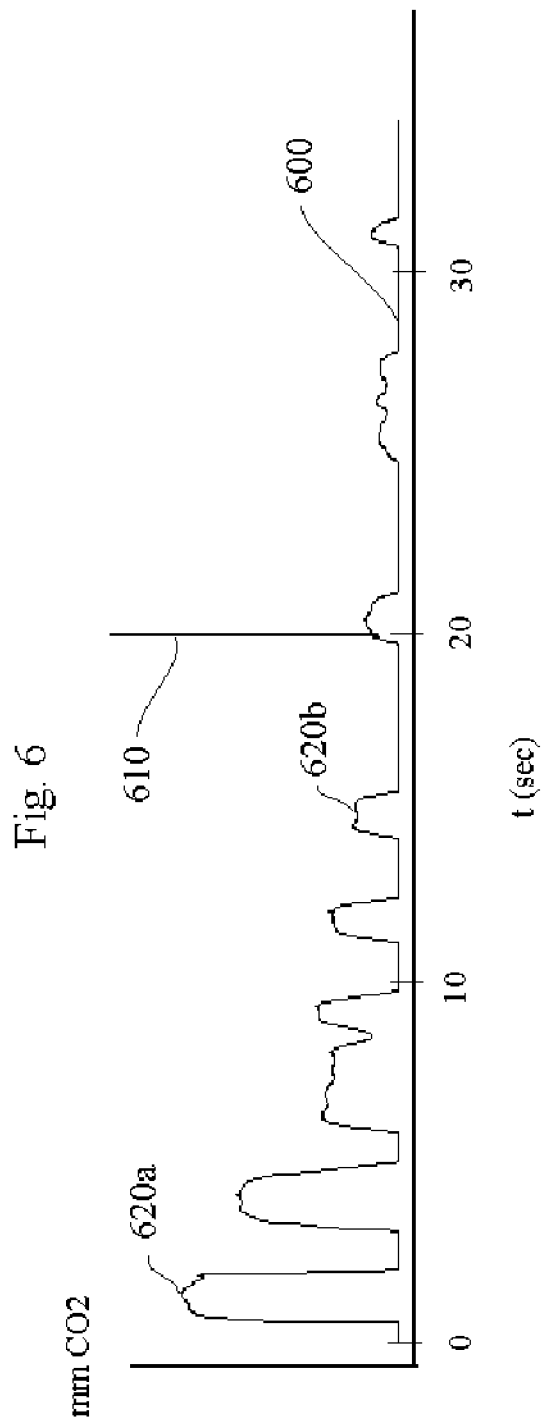
FIG. 6 illustrates a typical breath sequence of a CO2 signal for an improperly intubated patient.

Analyze therapy step 336 also detects an improper or dislodged placement of an endotracheal tube or advanced airway in the patient. FIG. 6 shows an example of a CO2 waveform 600 resulting from an improper endotracheal intubation. A few normal-looking true breaths 620a and 620b seen right after intubation due to CO2 in the stomach may lead to the erroneous belief that the placement is proper. The inventive method, however, continuously analyzes the sequence of true breaths for a predetermined period 610, in this case about 20 seconds, and provides corrective output guidance if an improper airway placement is detected.

Figure 7:
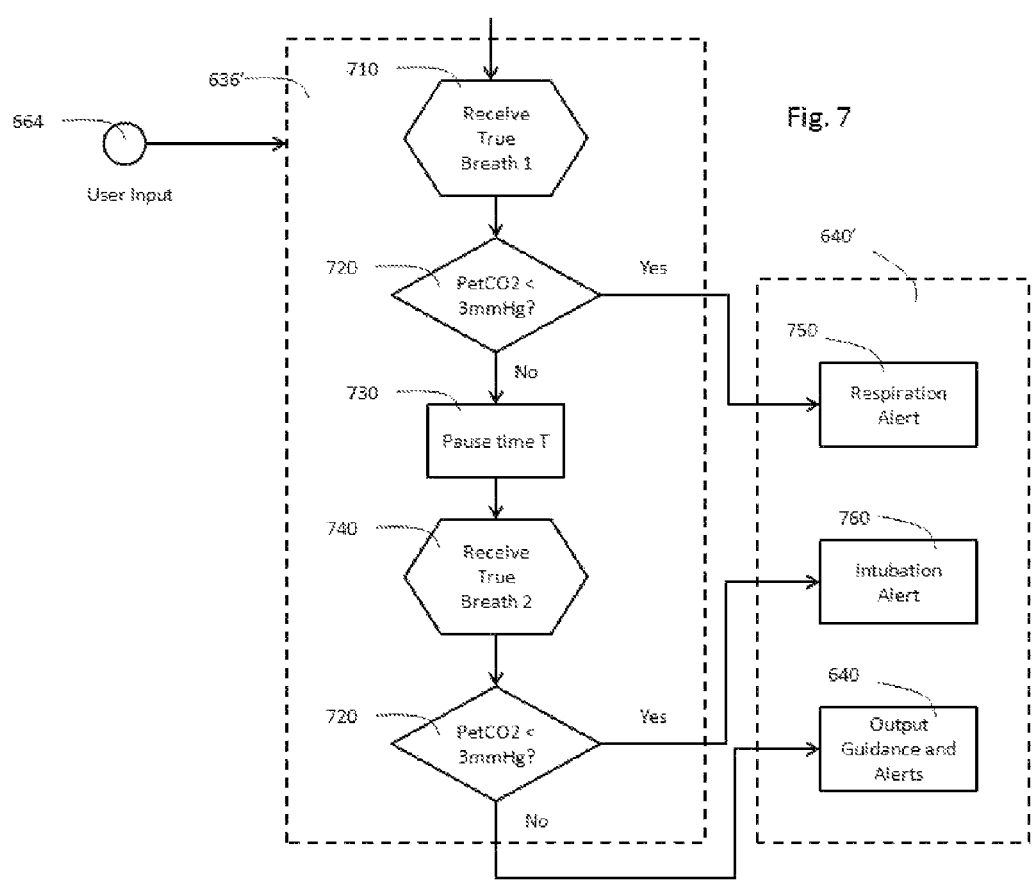
FIG. 7 illustrates a flow chart of the method of analyzing airway placement and providing user guidance in the case of an improper ETT or advanced airway placement.

The method of analyzing intubation therapy 636 is illustrated by FIG. 7. A first true breath is received at step 710 in which the etCO2 value is assessed. If the etCO2 value is initially less than a lower threshold, such as 3 mmHg, then step 720 sends an indication to an output guidance step 640 to provide a first respiration alert at step 750. The first respiration alert comprises guidance that etCO2 is low.

If, however, the first true breath etCO2 value is above the threshold, then a pause period is entered at step 730. After the pause period, such as 20 seconds, is concluded at step 730, a second true breath is received at step 740. The second true breath is then analyzed at step 720 in the same way as the first true breath. If the second etCO2 value has decayed over the time period to below the threshold, then a misplaced or dislodged endotracheal tube is indicated. Step 720 then provides an indication to output guidance step 640 such that an alert is generated at intubation alert step 760. If the second true breath continues to exceed the threshold value, then a third output guidance is generated at step 640 to indicate proper tube placement.

An alternative method for analyzing intubation therapy involves skipping the first step 720 of FIG. 7 altogether, and merely pausing for time T before analyzing a true breath. This alternative method is preferably begun by a signal from a user input 664 to analyze therapy step 636 which indicates the beginning of the intubation or airway placement period.

Now referring to FIG. 8, an analyzing therapy step 336 is described which analyzes the effectiveness of ongoing CPR. A true breath sequence and corresponding data is obtained in accordance with the foregoing method steps shown in FIG. 3. However, the analyzing therapy step 336 further uses a calculated respiration rate trend 820 and a detected gradual change of the etCO2 trend curve 800 to evaluate the effectiveness of CPR. In the FIG. 8 example, the respiration rate 820 lies below a high threshold limit of 15, while the etCO2 trend shows an increase over two minutes from 20 to 30 mmHg, or 50%. The respiration rate 820 with slowly increasing etCO2 indicates that the ongoing CPR is effective. In the effective case, a corresponding clinical guidance instruction is issued at the output step 340. On the other hand, if the respiration rate 820 and etCO2 trend parameters fail to indicate effective CPR, a corresponding clinical guidance instruction and/or an alert is issued at the output step 340.

The accuracy of the CPR effectiveness determination is improved with an indication that CPR compressions are occurring. Either a user input 364, information from a CPR sensor, or a stream of CPR artifact breath candidates 370 from step 334 may be used in the analyze therapy step 336 to ascertain ongoing CPR. Information from the CPR sensor can also be used in conjunction with the etCO2 algorithm at the classify breath step 333. Thus, the method can avoid a false CPR effectiveness guidance.

Figure 9:
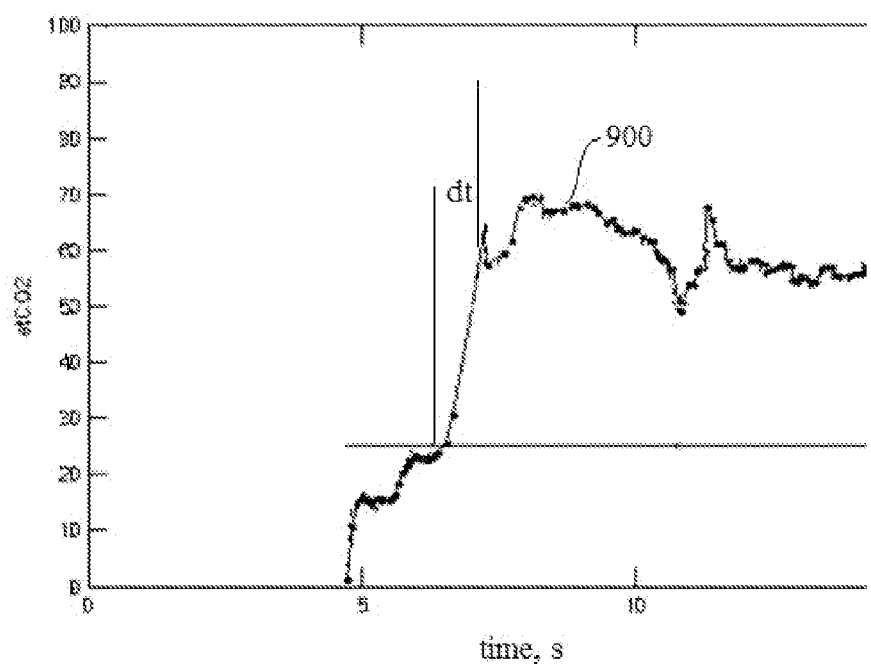
FIG. 9 illustrates in graphical form a measured etCO2 signal used in a method for determining ROSC.

Now referring to FIG. 9, an analyzing therapy step 336 is described which analyzes for the occurrence of the return of spontaneous circulation (ROSC). A true breath sequence and corresponding data is obtained in accordance with the foregoing method steps shown in FIG. 3. However, the analyzing therapy step 336 further uses a calculated respiration rate trend 820 and a detected rapid change of the etCO2 trend curve 900 to ascertain the occurrence of ROSC.

In the FIG. 9 example, the etCO2 trend shows a rapid increase from one true breath to the next true breath from 25 to 60 mmHg, which is greater than 50%. The rapidly increasing etCO2 indicates that the patient has begun to exchange CO2 naturally and without assistance. If ROSC is detected, a corresponding clinical guidance instruction is issued at the output step 340. On the other hand, if the etCO2 trend parameters fail to indicate ROSC, a corresponding clinical guidance instruction and/or an alert is issued at the output step 340. Also if the etCO2 trend shows a rapid drop, such as from 60 to 10 mmHg, then the loss of spontaneous circulation is indicated, and an alert to resume CPR may be provided.

The invention claimed is:

1. A carbon dioxide (CO2) monitoring system for use with patients undergoing patient therapy that includes application of cardiopulmonary resuscitation (CPR), comprising:
    a CO2 sensor which receives respiratory gases from a patient and senses CO2 content of the gases to produce CO2 measurement signals;
    a pre-processor which digitizes and stores the CO2 measurement signals as a CO2 signal stream;
    a breath candidate detector responsive to the CO2 signal stream which identifies a plurality of breath candidates;
    a breath characterizer which determines an end-tidal CO2 value for each breath candidate;
    a breath classifier which classifies each breath candidate as a true breath or an artifact generated as a result of an external CPR compression based on the breath candidate end-tidal CO2 value;
    a therapy analyzer, responsive to a plurality of true breaths from the breath classifier, which determines effectiveness of the patient therapy; and
    an output generator which provides an output instruction that instructs medical personnel to alter the patient therapy based on the determined effectiveness.

2. The CO2 monitoring system of claim 1, further comprising a filter which removes noise from the pre-processed CO2 signal stream.

3. The CO2 monitoring system of claim 1, wherein the breath characterizer further determines at least one of waveform baseline, waveform amplitude, waveform frequency, waveform slope, waveform rhythm, and waveform corners for each breath candidate, and further wherein the breath classifier classifies each breath candidate as a true breath or an artifact based on the at least one of waveform baseline, waveform amplitude, waveform frequency, waveform slope, waveform rhythm, and waveform corners for each breath candidate.

4. The CO2 monitoring system of claim 1, further comprising a therapy input to the therapy analyzer, wherein the therapy analyzer is further responsive to the therapy input to determine the effectiveness of the patient therapy.

5. The CO2 monitoring system of claim 1, wherein the therapy input comprises a switch which indicates an initiation of receiving respiratory gases at the CO2 sensor.

6. The CO2 monitoring system of claim 1, wherein the output instruction is responsive to an abnormal condition comprising one of no respiration received or erratic CO2 waveform.

7. The CO2 monitoring system of claim 1, wherein the output instruction is responsive to an abnormal condition comprising a decrease in the end-tidal CO2 values from the plurality of true breaths.

8. The CO2 monitoring system of claim 7, wherein the output instruction comprises a visual or audio advisory of the effectiveness of the CPR.

9. The CO2 monitoring system of claim 7, wherein the output instruction comprises one of check patient or adjust ventilator settings.

10. A method comprising:
    receiving, by a CO2 sensor, respiratory gases from a patient undergoing patient therapy that includes cardiopulmonary resuscitation (CPR);
    sensing, by the CO2 sensor, CO2 content of the gases to produce CO2 measurement signals;
    digitizing and storing, by one or more processors, the CO2 measurement signals as a CO2 signal stream;
    identifying, by one or more of the processors, a plurality of breath candidates responsive to the CO2 signal stream;
    determining, by one or more of the processors, an end-tidal CO2 value for each breath candidate;
    classifying, by one or more of the processors, each breath candidate as a true breath or an artifact generated as a result of an external CPR compression based on the breath candidate end-tidal CO2 value;
    determining, by one or more of the processors, effectiveness of the patient therapy responsive to a plurality of true breaths from the breath classifier; and
    altering the patient therapy based on the determined effectiveness.

11. The method of claim 10, further comprising applying filter to remove noise from the CO2 signal stream.

12. The method of claim 10, further comprising:
    determining, by one or more of the processors, at least one of waveform baseline, waveform amplitude, waveform frequency, waveform slope, waveform rhythm, and waveform corners for each breath candidate;
    wherein each breath candidate is classified as a true breath or an artifact based on the at least one of waveform baseline, waveform amplitude, waveform frequency, waveform slope, waveform rhythm, and waveform corners for each breath candidate.

13. The method of claim 10, wherein determining the effectiveness of the patient therapy is further based on a therapy input.

14. The method of claim 13, wherein the therapy input comprises a switch which indicates an initiation of receiving respiratory gases at the CO2 sensor.

15. The method of claim 10, further comprising outputting, by one or more of the processors, an output instruction to alter the patient therapy responsive to an abnormal condition comprising one of no respiration received or erratic CO2 waveform.

16. The method of claim 10, further comprising outputting, by one or more of the processors, an output instruction responsive to an abnormal condition comprising a decrease in the end-tidal CO2 values from the plurality of true breaths.

17. The method of claim 10, further comprising outputting, by one or more of the processors, a visual or audio advisory of effectiveness of the CPR.

* * * * *